США005565202A

United States Patent [19]
Witter

[11] Patent Number: 5,565,202
[45] Date of Patent: Oct. 15, 1996

[54] LOW ENHANCEMENT SEROTYPE 2 VACCINE FOR MAREK'S DISEASE

[75] Inventor: Richard L. Witter, Okemos, Mich.

[73] Assignee: The United States of America as represented by the Secretary of Agriculture, Washington, D.C.

[21] Appl. No.: 289,818

[22] Filed: Aug. 12, 1994

[51] Int. Cl.$^6$ .......................... A61K 39/255; A61K 39/12
[52] U.S. Cl. .................. 424/202.1; 424/93.6; 424/229.1; 424/816; 435/235.1; 435/237; 435/239
[58] Field of Search ............................. 424/202.2, 229.1, 424/816, 93.6; 435/235.1, 237, 239

[56] References Cited

U.S. PATENT DOCUMENTS

| | | | |
|---|---|---|---|
| 4,895,717 | 1/1990 | Witter | 424/229.1 |
| 4,895,718 | 1/1990 | Witter | 424/202.1 |
| 5,378,467 | 1/1995 | Bexendale | 424/202.1 |

OTHER PUBLICATIONS

Witter, et al. "Biological Diversity Among Serotype 2 Marek's disease Viruses", Avian Diseases 34:944–957 1990.
Witter, R. L. "Association in broiler chickens between Natural serotype 2 Marek's disease virus infection and leukosis condemnations". In:Proc. International Symposium or Marek's Disease–B. W. Calnek and J. C. Spencer, ed. American Association of Avian Pathologists, Kennett Square, PA pp. 545–554 1985.

Witter, Richard L., Abstract of oral Presentation, "Serotype 2 Marek's Disease Vaccines With Reduced Ability to Enhance Lymphoid Leukosis", World Veterinary Poultry Association, Australia, 16–19 Aug. 1993.

*Primary Examiner*—Anthony C. Caputa
*Attorney, Agent, or Firm*—M. Howard Silverstein; Randall E. Deck; John D. Fado

[57] ABSTRACT

A vaccine for Marek's disease using mutant strains of a serotype 2 field isolate, designated 471B/1, is disclosed. The mutant viruses, which are produced by serial passage of 471B/1 in cell culture, not only retain effective immunizing ability against Marek's disease virus, but which also exhibit reduced enhancement of lymphoid leukosis in comparison to non-passaged 471B/1 and conventional serotype 2 vaccines. These viruses or immunogenic components thereof can be formulated into monovalent and polyvalent vaccines.

15 Claims, No Drawings

LOW ENHANCEMENT SEROTYPE 2 VACCINE FOR MAREK'S DISEASE

BACKGROUND OF THE INVENTION

1. Field of the Invention

Marek's disease (MD), a highly prevalent and important lymphoproliferative disease of chickens, is controlled in commercial chickens by live virus vaccines consisting of attenuated or naturally avirulent MD-related herpesviruses. Although vaccination programs have been considered highly effective overall, the poultry industry continues to experience losses due to MD. Given the tendency of MD virus to became more virulent with time coupled with the economic pressures confronting the poultry industry, there is still a strong incentive to develop even more efficacious products that will protect better in the face of early challenge with very virulent field strains without causing adverse side effects. This invention relates to a novel vaccine against MD which does in fact provide superior protection and improved safety compared to certain existing commercial vaccines.

2. Description of the Prior Art

There are three distinct serotypes of MD virus found in chickens: (1) serotype 1, the oncogenic form responsible for the disease, including high- and low-virulence MD virus and their attenuated variants; (2) serotype 2, a nononcogenic MD virus; and (3) serotype 3, herpesvirus of turkeys (HVT).

The prototype MD vaccine consists of the serotype 3 virus originally isolated from turkeys as reported in Witter et al. [Am. J. Vet. Res. 31:525–538 (1970)] Okazaki et al. [U.S. Pat. No. 3,642,574]. Its lack of oncogenicity, self-limiting infection, good replication in vivo and in vitro, availability as cell-free and cell-associated preparations, and high protective efficacy have established HVT as a standard for MD vaccines throughout the world. A commonly used strain of HVT is FC126.

Vaccines produced from the naturally avirulent SB-1 strain [Schat et al., J. Natl. Cancer Inst. 60:1075–1082 (1978) and U.S. Pat. No. 4,160,024], an isolate of a serotype 2 MD virus, have been licensed in the United States since 1984. The SB-1 strain is poorly protective against the highly virulent Md5 strain. It is usually used in combination with HVT as a bivalent vaccine since the two viruses together produce greater protection than does either one alone [Schat et al., Avian Pathol. 11: 593–606 (1982); Witter, Avian Pathol. 11: 49–62 (1982), herein incorporated by reference]. This phenomenon has been termed "protective synergism." The SB-1+ HVT bivalent vaccine represents about 18% of the United States market for MD vaccines at present and is considered to be among the most efficacious of the various MD products available. However, sporadic losses occur despite its use.

Another MD vaccine produced from strain CVI988 clone C (CVI988/C) bas been licensed for commercial use in the United States. This vaccine is a mildly virulent serotype 1 MD virus attenuated by serial passage in tissue culture and has been reported by deBoer et al. [Arian Dis. 30: 276–283 (1986)]. A further passaged derivative of CVI988/C, identified as CVI988/C/R6, has also been described by de Boer et al. [Advances in Marek's Disease Research, pp. 405–413 (1988)]. More recently, the original low-passage strain, designated CVI988/Rispens, which has been in commercial use in other countries for a number of years, was found to be highly effective against challenge with several very virulent MD virus strains by Witter et al. [4th Int'l Syrup. Marek's Disease, pp. 315–319 (1992)].

An experimental vaccine derived from Md11, a very virulent serotype 1 MD field isolate, was reported by Witter, supra. Md11 was attenuated by 75 serial passages in cell culture, and the resultant vaccine designated Md11/75C. This vaccine has been shown to provide good protection against challenge with Md5 and most other highly virulent MD viruses tested; but it was less efficacious against challenge with the JM/102W strain, a prototype MD virus effectively protected against by HVT and SB-1 vaccines. Furthermore, its efficacy was consistently lower in chicks with HVT antibody.

In U.S. Pat. No. 4,895,717, Witter disclosed a revertant derivative of Md11/75C which was referred to as Md11/75C/R2. Md11/75C/R2 was shown to be superior to several other monovalent vaccines and was the equal of a bivalent (HVT+SB-1) vaccine [Witter, Avian Dis. 31:752–765 (1987)]. However, the inherent pathogenicity of serotype 1 viruses and the potential of attenuated strains to revert to greater pathogenicity (Witter et al., Avian Pathol. 13:75–92 (1984)] are factors to be considered in the licensing of such products. A clone derived from further passages of the Md11/75C/R2 strain, designated Md11/75C/R2/23 (or R2/23), was found by Witter et al. [Avian Dis., 35:877–891 (1991)] to possess the highly protective nature of the parent strain without its residual pathogenicity.

Witter also described another MD vaccine derived from 301B/1, a nonpathogenic serotype 2 field isolate, in U.S. Pat. No. 4,895,718, the contents of which are incorporated by reference herein. Strain 301B/1 possessed superior replicative ability to SB-1, as well as greater protectivity against challenge to viruses.

Thus, although HVT, SB-1, CVI988/C, Md11/75C, Md11/75C/R2, CVI988/C/R6, CVI988/Rispens, MD11/75C/R6/23 and 301B/1 are all effective against certain MD viruses, none of these vaccines protect optimally against all MD challenge viruses in all chickens. In an effort to avert any large-scale outbreaks of MD in the future, the search for improved vaccines has continued.

Still other concerns have arisen over the use of same MD vaccines. As indicated, bivalent vaccines composed of MD virus serotypes 2 and 3 are currently widely used in the U.S. and have provided excellent protection against very virulent MD strains. However, use of such vaccines containing serotype 2 MD virus may lead to increased mortality from another disease, lymphoid leukosis, as reported by Bacon et al. [J. Virol., 63:504–512 (1989)]. This enhancement of lymphoid leukosis in avian eukosis virus infected chickens resulting i from vaccination with products containing serotype 2 MD virus has been an unfortunate deterrent to their expanded use. The need exists for an effective serotype 2 MD vaccine which does not enhance lymphoid leukosis.

SUMMARY OF THE INVENTION

I have now discovered a novel vaccine for Marek's disease using mutant strains of a serotype 2 field isolate, designated 471B/1. In contrast to other serotype 2 MD vaccines, I have unexpectedly found that mutants of Marek's disease virus strain 471B/1 may be produced in vitro by serial passage of 471B/1 in cell culture which not only retain effective immunizing ability against MD virus, but also exhibit reduced enhancement of lymphoid leukosis in comparison to non-passaged 471B/1 and other conventional serotype 2 vaccines. Suitable formulations of the vaccine for use in chickens include an effective immunization dosage of this novel viral agent with a pharmaceutically acceptable carrier or diluent.

In accordance with this discovery, it is an object of the invention to provide a novel, highly protective, serotype 2 vaccine against MD in chickens, which is characterized by reduced enhancement of lymphoid leukosis compared to other serotype 2 vaccines.

It is also an object of i the invention to provide both monovalent and polyvalent vaccines against MD which are at least as efficacious as those presently in commercial use.

It is another object of the invention to improve the viability and productivity of chickens, particularly broilers and layers, and to reduce economic losses in the poultry industry caused by MD.

Other objects and advantages of this invention will become readily apparent from the ensuing description.

DEPOSIT OF BIOLOGICAL MATERIAL

Mutant serotype 2 Marek's disease virus clone 471B/1(p33) has been deposited under the provisions of the Budapest Treaty in the American Type Culture Collection in Rockville, Md. 20852, on Aug. 10, 1994 and has been assigned Accession No. ATCC VR 2472.

DETAILED DESCRIPTION OF THE INVENTION

As used herein, "mutant" refers to any stable virus derived or produced by serial passage whose functional properties are different from the parent strain.

"Vaccine" is defined herein in its broad sense to refer to any type of biological agent in an administratable form capable of stimulating an mine response in an animal inoculated with the vaccine. For purposes of this invention, the vaccine my comprise either the virus itself or an immunogenic (antigenic) component of the virus. The vaccine my also be produced from a vector having inserted therein a gene which encodes an immunogenic component of the virus.

As previously mentioned, the mutant clones of this invention are derived from a MD serotype 2 virus strain designated 471B/1. They were obtained by serially passing 471B/1 in cell culture using techniques conventional in the art. Briefly, the virus may be serially passaged by inoculating susceptible cell cultures, such as chicken embryo fibroblast (CEF) prepared from 8-day old chicken embryos and grown in Leibovitz-McCoy medium with 1% calf serum in a humidified atmosphere with 5% carbon dioxide at 38° C. The culture medium is changed at 2–3 day intervals. At about 7 days, when cytopathic effects of the virus are well developed, the cells are released from the culture dish using trypsin, washed in culture medium, and seeded into new culture dishes containing nearly confluent monolayers of chicken embryo cells. This passage procedure is repeated until the requisite number of passages has been achieved.

The 471B/1 virus should be passaged a sufficient number of times such that enhancement of lymphoid leukosis in treated chickens is substantially reduced in comparison to the non- or low-passaged 471B/1. However, because excessively high passage decreases the protective ability of the virus, it should not be passed so many times that it loses immunizing ability in chickens against challenge with virulent MD virus strains in comparison to untreated birds. I have generally found that serial passage of strain 471B/1 results in a significant reduction or attenuation of lymphoid leukosis enhancement by about passage number 33 (referred to as p33). Conversely, mutants produced by continued serial passage beyond 50 times exhibit steadily decreasing protective ability, although it is substantially retained through passage number 50 (p50). Serial passage of strain 471B/1 an intermediate number of times, particularly between about 37 and 43 times, yields mutants possessing an optimal equilibrium between protective ability and reduction of lymphoid leukosis enhancement. Accordingly, without being limited thereto, preferred viral agents of this invention are mutants produced by serially passing strain 471B/1 in cell culture between about 33 and 50 times, (p33) to (p50), and particularly between about 37 and 43 times, (p37) to (p43).

The mutant produced by serial passage of 471B/1 in cell culture 33 times, designated 471B/1(p33), has been deposited under the Budapest Treaty, as noted hereinabove. Strain 471B/1(p33) may itself be incorporated into the vaccine of this invention, or the virus may be used as the master seed for production of further serially passed mutants, particularly (p37) to (p43). Techniques for this further serial passage are the same as those described above. Compared to other commercial serotype 2 viruses, the viruses of this invention are characterized by favorable replicative ability both in vivo and in vitro, and also superior protectivity against challenge viruses.

A cell-associated vaccine can be prepared directly from in vitro culture of the live viral agents in a suitable cloning medium, such as chicken embryo fibroblasts as described by Witter [4,895,718, previously incorporated by reference]. Alternatively, to prepare cell-free virus inocula, cells from infected host tissue or cell culture are sonicated or otherwise disrupted as previously described. The cellular debris is removed by centrifugation and the centrifugate recovered as the inoculum. It is also an embodiment of the invention to prepare vaccines from the killed virus or from immunogenic components separated from the virus. For example, a subunit vaccine can be prepared by separating from the killed virus one or more purified viral proteins identified as having immunogenic properties.

It is envisioned within the ambit of the invention that the gene or genes encoding the immunogenic component or components responsible for the protective ability of the viruses could be inserted into a suitable vector system by recombinant techniques as known in the art. The methodology involving recombinant DNA techniques has now become routine in science and has been successfully demonstrated in analogous applications [E. Paoletti et al., *Proc. Natl. Acad. Sci. U.S.A.* 81: 193–197 (1984)]. Specifically, the process would first involve the identification of proteins or other components of the clones that are critical to the induction of protective immunity. Next, specific regions of the viral genome (genes) along with an endogenous promoters would be identified and characterized through mapping with restriction endonucleases and determination of the nucleotide sequences. The identified gene or genes would then be spliced into expression vectors such as bacterial plasmids (to produce a killed protein product) or live viruses such as avian herpesviruses or avian poxviruses (to produce a live recombinant DNA vaccine virus). Other types of expression vectors could also be used. Once properly constructed with the necessary promoter sequences, the expression vector will produce the product of the inserted gene; namely, the critical immunizing protein or proteins of the virus. If produced by a vector grown in vitro, the immunizing protein will be obtained from the culture medium, purified, and used with appropriate adjuvants and diluents as a killed vaccine for the immunization of chickens. Other vectors, chosen for their natural infectivity for chickens, will be inoculated directly into chickens as a recombinant live virus vaccine. The vaccine will then produce the immunizing protein in vivo, thus causing protection directly and without the need for additional inoculations.

Thus, it is apparent from the above discussion that viral agents contemplated within the scope of the invention include mutants of strain 471B/1 which are derived through serial passage and which retain the ability to elicit an immune response to a MD virus but exhibit reduced enhancement of lymphoid leukosis in chickens. Viral agents that are particularly contemplated include viruses having the essential identifying characteristics of strain 471B/1(p33) and mutants which have been produced by further serial passage of 471B/1(p33). Also contemplated as the viral agent are antigens which are effective to elicit an immune response in chickens to MD virus, whether those antigens have been derived directly from the viruses or their clones, or expressed by a recombinant virus as described, supra.

The viral agent is prepared for administration by formulation in an effective immunization dosage with a pharmaceutically acceptable carrier or diluent, such as physiological saline or tissue culture medium. The expression "effective immunization dosage" is defined as being that amount which will induce immunity in a chicken against challenge by a virulent strain of MD. Immunity is considered as having been induced in a population of chickens when the level of protection for the population is significantly higher than that of an unvaccinated control group. One measure of the level of protection is the protective index (PI), which is calculated as the MD in unvaccinated, MD virus challenged controls minus the MD in vaccinated, MD virus challenged groups, and the difference divided by the percent MD in unvaccinated, MD virus challenged controls, with the result multiplied by 100. Typically, the vaccine will contain at least about 1500 PFU (plaque-forming units) of the virus, and preferably between 2000 and 5000 PFU. The vaccine can be effectively administered anytime after the chicken attains immunocompetence, which is at about the 18th day of incubation (3 days prehatch); but it is normally administered by inoculation within 24–48 hrs after hatching.

Appropriate adjuvants as known in the art may also be included in the vaccine formulation. In many cases, the vaccinal efficacy can be enhanced by combining the 471B/1 mutants with other viral agents into bivalent or polyvalent vaccines. In a particularly preferred embodiment, the 471B/1 mutants are combined with HVT as a bivalent vaccine as described by Schat et al. or Witter (ibid).

The following examples are intended only to further illustrate the invention and are not intended to limit the scope of the invention which is defined by the claims.

EXAMPLE 1

Lymphoid Leukosis enhancement. In two separate trials, seven serotype 2 MD virus strains, SB-1, 301B/1, HN-1, 281MI/1, 287C/1, 298B/1, 401/1, 437A/1 and 471B/1, were examined for their ability to enhance lymphoid leukosis (LL) in susceptible, avian leukosis virus (ALV) infected chicks. The chickens used in the first trial were White Leghorn chickens obtained as fertile hatching eggs from a commercial breeder. The parent females were vaccinated against MD and were presumed to have been naturally exposed to ALV. The chickens used for the second trial were $F_1$ progeny (15×7) of Regional Poultry Laboratory line $15I_5$ males and line $7_1$ females. The parent females were unvaccinated breeder hens that were free of antibodies to MD virus ALV, and HVT and the progeny chickens were considered negative for maternal antibodies (ab-). In the first trial, each chicken was inoculated intraabdominally at 1 day of age with 2000 PFU of SB-1, SB-1+ FC126 (HVT), 301B/1 or 301B/1+ FC126 (1000 PFU of each component virus) and placed in a vinyl canopy, positive pressure isolator. At 1 day post vaccination, each chicken was challenged with $10^4$ infectious units of an ALV strain, RPL42. The birds were held for about 27 weeks post challenge, killed and necropsied, and the presence of LL was recorded. Birds dying during the experiment were examined for LL. The percent LL was calculated as the number of chickens with gross LL lesions divided by the number of chickens at risk with the result multiplied by 100. Substantially the same procedure was repeated in the second experiment except that the chickens were inoculated with 2000 PFU HN-1(p25), SB-1(p23), 281MI/1(p20), 287C/1(p19), 298B/1(p24), 301B/1(p11) 401/1(p12), 437A/1(p12) and 471B/1(p14), wherein the number in parentheses refers to the passage level of the vaccines. Positive and negative controls, challenged with ALV and not receiving any challenge virus, respectively, were included.

Data were analyzed by Bonferroni's modification of Student's t-test, in which the value of t for two groups was based on a variance computed from all groups, and the values of t required for statistical significance were adjusted for the number of paired observations made.

The results of each experiment are shown in Tables 1 and 2, respectively. The results show that the MD serotype 2 strains differed in their ability to enhance LL, but that only one, HN-1, did not enhance LL.

EXAMPLE 2

Preparation of Passaged Viral Stocks. Virus stocks useful as vaccines in accordance with this invention were produced from MD serotype 2 virus strain 471B/1, a previously discovered field isolate, by serial passage of 471B/1 in chicken embryo fibroblast (CEF) culture. At selected passage levels between 17 and 60, virus stocks were prepared and evaluated as described in the following Examples. A seed stock, designated 471B/1(p33) was preserved at the 33rd passage by cryopreservation as described by Witter [U.S. Pat. No. 4,895,718], and deposited in the American Type Culture Collection under Accession No. ATCC VR 2472.

EXAMPLE 3

Effect of passage on LL enhancement. Three serially passaged strains from Example 2, 471B/1(p17), (p27) and (p40), were compared for enhancement of LL. The procedure was essentially the same as described in Example 1 (Trial 2) except that chickens were examined at 22 weeks.

As shown in Table 3, mortality from LL decreased with increasing passage number of the vaccinating strain. Although vaccination with 471B/1(p17) and (p27) increased or enhanced the incidence of LL, by passage number 40, this enhancement was substantially reduced and did not differ significantly from those in unvaccinated controls.

EXAMPLE 4

Protection against MD. Strain 471B/1 (p40), which showed a substantial reduction in enhancement of LL in Example 3, was assayed for protective efficacy against challenge with virulent MD virus. Other commercial vaccine strains were also examined for comparative purposes. The chickens were 15×7 as in Example 1, except they were obtained from breeder hens vaccinated with all three MD serotypes, i.e., Md11/75C (serotype 1), SB-1 (serotype 2), and FC126 (serotype 3) at a dose of at least 1000 PFU for each virus and were considered positive for maternal antibodies (ab+). Each chicken was inoculated at 1 day of age with 2000 PFU of 471B/1(p40), FC126, 471B/1(p40)+FC126 (HVT), or 301B/1+FC126 (2000 PFU of each) and placed in a modified Horsfall-Bauer isolator. At 5 days post vaccination, each chicken was challenged with 500 PFU of Md5 virus. The birds were held for about 56 days post challenge, killed and necropsied, and the presence of gross lesions was recorded. Birds dying during the experiment were examined for gross lesions. The birds considered to be at risk were those positive for MD lesions plus those survivors without lesions. The percent protection was calculated as the percent MD in unvaccinated, challenged controls minus the percent MD in vaccinated, challenged groups divided by the percent MD in unvaccinated, challenged controls multiplied by 100.

The results are reported in Table 4. Strain 471B/1(p40) provided effective protection and was not statistically different from 301B/1 when both were combined with HVT as a bivalent vaccine.

EXAMPLE 5

Further analysis of LL enhancement and protection against MD. A variety of the passaged stocks from Example 2 were compared for enhancement of LL and for protective efficacy against challenge with virulent MD virus. In a first experiment, reduction of enhancement of LL was determined using essentially the same procedure as Example 3 except that strains 471B/1(p17), (p30), (p33), (p37) and (p40) were used as vaccine viruses. Protective efficacy against MD was determined in a second experiment using essentially the same procedure as Example 4 except that the above-mentioned passaged strains plus (p43), (p47), (p50) and (p60) were used in combination with FC126 (HVT).

The results of the two experiments are shown in Tables 5 and 6. While (p17) and (p30) did not exhibit reduced enhancement of LL and none showed complete absence of enhancement, all passaged strains beyond and including p33 showed a substantial reduction of LL enhancement. Protective efficacy was substantially retained through passage number 50, protection decreased thereafter.

EXAMPLE 6

Comparative protection against MD. Another experiment was conducted to compare the protective efficacy of (p33) and (p40) with other serotype 1 and 2 vaccines including commercial vaccines. The procedure of Example 4 was essentially repeated except that chicks were vaccinated with strains 471B/1(p33), 471B/1(p40), 471B/1(p33)+FC126 (HVT), 471B/1(p40)+FC126, FC126, SB-1+FC126, 301B/1+FC126, CVI988/Rispens, and R2/23 (serotype 1).

The results are shown in Table 7. Both 471B/1(p33) and (p40) gave good results and when used with HVT did not differ significantly from other prototype bivalent serotype 2 vaccines or serotype 1 vaccines.

It is understood that the foregoing detailed description is given merely by way of illustration and that modification and variations may be made therein without departing from the spirit and scope of the invention.

TABLE 1

LL Enhancement by SB-1 and 301B/1

| Isolate | ALV | Chicks | % LL (27 wks) |
| --- | --- | --- | --- |
| SB-1 | + | 31 | 50a |
| SB-1 + HVT | + | 34 | 76a |
| 301B/1 | + | 33 | 67a |
| 301B/1 + HVT | + | 25 | 88a |
| None | + | 24 | 24b |

Commercial WL chickens, RPL42 @ 1 day

TABLE 2

Augmentation of Lymphoid Leukosis

| | | | % LL (18 wks) | |
| --- | --- | --- | --- | --- |
| Isolate | ALV | Chicks | Mort | Total |
| HN-1 | + | 34 | 2.9a | 35.3a |
| SB-1 | + | 30 | 30.0b | 83.3b |
| 287C/1 | + | 28 | 28.6b | 89.3b |
| 301B/1 | + | 33 | 21.2b | 81.8b |
| 401/1 | + | 33 | 12.1b | 84.8b |
| 437A/1 | + | 35 | 31.4b | 82.9b |
| 471B/1 | + | 34 | 26.5b | 67.6b |
| None | + | 32 | 0.0a | 31.3a |
| None | − | 34 | 0.0 | 0.0 |

TABLE 3

Effect of Strain and Passage

| | | | | % LL (22 wks) | |
| --- | --- | --- | --- | --- | --- |
| Isolate | Pass | ALV | Chicks | Mort | Total |
| 471B/1 | 17 | + | 34 | 91.2b | 97.1a |
| | 27 | + | 33 | 69.7b | 93.9a |
| | 40 | + | 34 | 47.1a | 94.1a |
| None | | + | 32 | 37.5a | 96.9a |
| None | | − | 33 | 0.0 | 0.0 |

TABLE 4

Protection Against MD by Low-Enhancement Strain 471B/1

| Strain | # Birds | % MD | PI |
| --- | --- | --- | --- |
| 471B/1 (p40) | 34 | 64.7 | 25a |
| 471B/1 (p40) + FC126 | 32 | 18.8 | 74bc |
| Controls: | | | |
| FC126 | 33 | 63.6 | 26a |
| 301B/1 + FC126 | 33 | 12.1 | 81c |
| None | 33 | 93.9 | |

TABLE 5

LL Enhancement by 471B/1

| Strain | Pass | ALV | # | % LL Mort | % LL Total | % Metastasis |
| --- | --- | --- | --- | --- | --- | --- |
| 471B/1 | 17 | + | 33 | 42.4* | 97.0* | 78.8* |
| | 30 | + | 35 | 40.0* | 82.9 | 60.0* |
| | 33 | + | 33 | 24.2 | 72.7 | 51.5* |
| | 37 | + | 32 | 21.9 | 59.4 | 43.8* |
| | 40 | + | 35 | 11.4 | 68.6 | 37.1* |

TABLE 5-continued

LL Enhancement by 471B/1

| Strain | Pass | ALV | # | % LL Mort | % LL Total | % Metastasis |
| --- | --- | --- | --- | --- | --- | --- |
| None | | + | 34 | 8.8 | 58.8 | 11.8 |
| None | | − | 35 | 0.0 | 0.0 | 0.0 |

\* = greater than ALV alone (P < 0.05)

TABLE 6

Protection Against MD By Various Passage Levels of 471B/1 Virus in Combination With HVT

| Vaccine Strain | # Chicks | % MD | PI |
| --- | --- | --- | --- |
| 471B/1 (p17) + FC126/2 | 16 | 56.3 | 44ab |
| 471B/1 (p37) + FC126/2 | 17 | 29.4 | 71a |
| 471B/1 (p40) + FC126/2 | 17 | 41.2 | 59a |
| 471B/1 (p43) + FC126/2 | 16 | 37.5 | 63a |
| 471B/1 (p47) + FC126/2 | 16 | 50.0 | 50a |
| 471B/1 (p50) + FC126/2 | 16 | 50.0 | 50a |
| 471B/1 (p60) + FC126/2 | 17 | 88.2 | 12b |
| Controls: | | | |
| FC126/2 | 17 | 58.8 | 41a |
| None | 17 | 100.0 | |

TABLE 7

Protection by 471B/1

| Strain | Birds | % MD | PI |
| --- | --- | --- | --- |
| 471B/1 (p33) | 51 | 62.7 | 37a |
| 471B/1 (p40) | 51 | 64.7 | 35a |
| 471B/1 (p33) + FC126 | 51 | 21.6 | 78bc |
| 471B/1 (p40) + FC126 | 51 | 23.5 | 76bc |
| FC126 | 50 | 82.0 | 18a |
| FC126 + SB-1 | 50 | 18.0 | 82c |
| FC126 + 301B/1 | 47 | 10.6 | 89c |
| CVI988/Rispens | 50 | 10.0 | 90c |
| R2/23 | 47 | 38.3 | 62b |
| None | 51 | 100.0 | |

Md5 Challenge at 5 pvd (summary of 3 trials)

I claim:

1. A viral agent selected from the group consisting of a serotype 2 Marek's Disease virus having all the identifying characteristics of strain 471B/1 serially passaged in cell culture 33 times, assigned Accession No. VR 2472, and mutants thereof, said mutants are produced by further serial passage of virus strain 471B/1 serially passaged in cell culture 33 times, assigned Accession No. VR 2472, said viral agent retaining the ability to elicit an immune response to Marek's disease virus.

2. A viral agent as described in claim 1 wherein said mutants have been produced by serial passages up to about 50 times.

3. A serotype 2 Marek's disease virus as described in claim 1 comprising said mutants produced by serial passages between about 37 and 43 times.

4. A vaccine comprising: (1) an effective immunization dosage of viral agent, wherein said viral agent is selected from the group consisting of serotype 2 Marek's Disease virus strain 471B/1 serially passaged in cell culture 33 times, assigned Accession No. VR 2472 and further mutants thereof produced by serial passage in cell culture of said strain 471B/1 serially passaged in cell culture 33 times, wherein said viral agent retains the ability to elicit an immune response to a Marek's disease virus but exhibits reduced enhancement of lymphoid leukosis in chickens, and (2) a pharmaceutically acceptable carrier or diluent.

5. A vaccine as described in claim 4 wherein said mutants have been produced by serial passages up to about 50 times.

6. A vaccine as described in claim 4 wherein said viral agent comprises said mutants produced by serial passages between about 37 to 43 times.

7. A vaccine as described in claim 4 wherein said viral agent is associated with the cells of said culture.

8. A vaccine as described in claim 4 wherein said viral agent is in a cell-free preparation.

9. A vaccine as described in claim 4 further comprising a second viral agent which is of the herpesvirus of turkeys type.

10. A method for protecting a chicken against Marek's disease comprising inoculating said chicken with a vaccine comprising an effective immunization dosage of viral agent in a pharmaceutically acceptable carrier or diluent, wherein said viral agent is selected from the group consisting of serotype 2 Marek's Disease virus strain 471B/1 serially passaged in cell culture 33 times, assigned Accession No. VR 2472 and further mutants thereof produced by serial passage in cell culture of said strain 471B/1 serially passaged in cell culture 33 times, wherein said viral agent retains the ability to elicit an immune response to a Marek's disease virus but exhibits reduced enhancement of lymphoid leukosis in chickens.

11. A method as described in claim 10 wherein said mutants have been produced by serial passages up to about 50 times.

12. A method as described in claim 10 wherein said viral agent comprises said mutants produced by serial passages between about 37 to 43 times.

13. A method as described in claim 10 wherein said viral agent is associated with the cells of said culture.

14. A method as described in claim 10 wherein said viral agent is in a cell-free preparation.

15. A method as described in claim 10 wherein said vaccine further comprises a second viral agent which is of the herpesvirus of turkeys type.

\* \* \* \* \*